United States Patent
Harrison

(10) Patent No.: US 8,030,260 B2
(45) Date of Patent: Oct. 4, 2011

(54) PRE-SHAVE COMPOSITIONS AND METHODS OF USING SAME

(75) Inventor: James Jeffries Harrison, West Hills, CA (US)

(73) Assignee: Chemsil Silicones, Inc, Chatsworth, CA (US)

( * ) Notice: Subject to any disclaimer, the term of this patent is extended or adjusted under 35 U.S.C. 154(b) by 562 days.

(21) Appl. No.: 11/879,039

(22) Filed: Jul. 13, 2007

(65) Prior Publication Data

US 2008/0057017 A1 Mar. 6, 2008

Related U.S. Application Data

(63) Continuation-in-part of application No. 11/389,661, filed on Mar. 24, 2006, now Pat. No. 7,863,230, which is a continuation-in-part of application No. 11/089,953, filed on Mar. 25, 2005, now Pat. No. 7,405,186.

(51) Int. Cl.
*C10M 107/34* (2006.01)
*C07D 207/26* (2006.01)
*A61K 8/18* (2006.01)

(52) U.S. Cl. ............... 508/579; 508/268; 424/70.15; 424/70.11

(58) Field of Classification Search .......... 508/268, 508/579; 424/70.15, 70.11
See application file for complete search history.

(56) References Cited

U.S. PATENT DOCUMENTS

| | | | |
|---|---|---|---|
| 3,954,960 A | 5/1976 | Valan | |
| 3,980,571 A | 9/1976 | Marx | |
| 4,415,548 A | 11/1983 | Reddy | |
| 4,578,203 A | 3/1986 | Franz et al. | |
| 4,781,847 A | 11/1988 | Weitz | |
| 5,468,401 A | 11/1995 | Lum et al. | |
| 5,512,289 A | 4/1996 | Tseng et al. | |
| 5,525,336 A | 6/1996 | Green et al. | |
| 5,635,169 A | 6/1997 | Blankenburg et al. | |
| 5,696,061 A | 12/1997 | Walsh | |
| 5,711,896 A | 1/1998 | Kaimai | |
| 5,747,043 A | 5/1998 | Ginoux et al. | |
| 5,785,054 A * | 7/1998 | Kelly ...................... | 128/842 |
| 5,885,591 A | 3/1999 | Ahmad et al. | |
| 5,935,636 A | 8/1999 | Nishimoto et al. | |
| 5,948,420 A | 9/1999 | Ferhut et al. | |
| 5,980,477 A | 11/1999 | Kelly | |
| 5,993,854 A | 11/1999 | Needleman et al. | |
| 6,054,422 A | 4/2000 | Ward et al. | |
| 6,123,933 A | 9/2000 | Hayama et al. | |
| 6,139,848 A | 10/2000 | Ahmad et al. | |
| 6,180,124 B1 | 1/2001 | Ohta et al. | |
| 6,196,227 B1 | 3/2001 | Tsushima | |
| 6,287,580 B1 | 9/2001 | Gott et al. | |
| 6,440,429 B1 | 8/2002 | Torizuka et al. | |
| 6,495,150 B2 | 12/2002 | Bekele | |
| 6,534,090 B2 | 3/2003 | Puthli et al. | |
| 6,548,456 B1 | 4/2003 | Mulder et al. | |
| 6,630,163 B1 | 10/2003 | Murad | |
| 6,663,855 B2 | 12/2003 | Frechet et al. | |
| 6,673,374 B2 | 1/2004 | Murad | |
| 6,685,925 B2 | 2/2004 | Frechet et al. | |
| 6,709,648 B2 | 3/2004 | Sako et al. | |
| 6,752,998 B2 | 6/2004 | Verdrel-Lahaxe et al. | |
| 7,005,408 B2 * | 2/2006 | Ahmad et al. ............ | 508/219 |
| 7,086,403 B2 | 8/2006 | Harrison et al. | |
| 2003/0059489 A1 * | 3/2003 | Letourneau et al. ....... | 424/776 |
| 2003/0108502 A1 * | 6/2003 | Uchida et al. ............ | 424/70.11 |
| 2003/0207772 A1 | 11/2003 | Ahmad et al. | |
| 2003/0211161 A1 | 11/2003 | Ahmad et al. | |
| 2003/0232090 A1 | 12/2003 | Ahmad et al. | |
| 2004/0037911 A1 * | 2/2004 | Letourneau et al. ....... | 424/776 |
| 2004/0138074 A1 | 7/2004 | Ahmad et al. | |
| 2004/0167039 A1 | 8/2004 | Ahmad et al. | |
| 2004/0185065 A1 | 9/2004 | Ahmad et al. | |
| 2005/0241982 A1 | 11/2005 | Muni et al. | |

OTHER PUBLICATIONS

USPTO Office Action dated Jul. 12, 2007 in U.S. Appl. No. 11/089,953, filed Mar. 25, 2005.

* cited by examiner

*Primary Examiner* — Glenn A Caldarola
*Assistant Examiner* — Vishal Vasisth
(74) *Attorney, Agent, or Firm* — Stout, Uxa, Buyan & Mullins; Carlos A. Fisher; Frank J. Uxa

(57) ABSTRACT

Preshave compositions and methods of using such compositions are disclosed. The present preshave compositions include at least about 50% by weight of a polyalkylene glycol component, preferably including at least two portions of different molecular weights, and an additional component in an amount effective to benefit the area of the body to be shaved. The present compositions are advantageously substantially clear and are substantially anhydrous and generate heat when contacted with water.

35 Claims, No Drawings

PRE-SHAVE COMPOSITIONS AND METHODS OF USING SAME

RELATED APPLICATION

This application is a continuation-in-part of U.S. patent application Ser. No. 11/389,661, filed Mar. 24, 2006, now U.S. Pat. No. 7,863,230, which is a continuation-in-part of U.S. patent application Ser. No. 11/089,953 now U.S. Pat. No. 7,405,186, filed Mar. 25, 2005, the disclosure of each of which is hereby incorporated in its entirety herein by this reference.

BACKGROUND OF THE INVENTION

The present invention relates to pre-shave compositions and methods of making and using such products. More particularly, the invention relates to warming preshave compositions and methods of using such compositions.

Personal lubricants, for example, in the form of pourable liquids, pourable low viscosity thixotropic gels, jellies and the like, are known and are useful for providing lubricity to various parts of the human body, for example, to mucous membranes, such as the oral, rectal, vaginal and the like mucosa. For example, see Ahmad et al U.S. Pat. No. 5,885,591, the disclosure of which is incorporated in its entirety herein by reference. Certain such lubricants have been proposed which generate heat or warming when placed in contact with the human body.

Preshave compositions for facilitating the shaving of hair, such as facial hair, leg hair and underarm hair, are well known. Typically, such compositions have been applied as liquids to the skin and hair shortly before shaving. To aid in shaving, some of these compositions have lubricated the skin, removed oils and moisture from the hair and skin, and/or caused the hair to rise and protrude temporarily from the skin. For example, see Scodari U.S. Pat. No. 4,457,912, as well as U.S. Pat. No. 6,861,556 and U.S. Pat. No. 7,008,628, the disclosure of each of which is incorporated in its entirety herein by reference.

There continues to be a need for new preshave compositions, including warming preshave compositions, and methods of using such compositions.

SUMMARY OF THE INVENTION

New preshave compositions and methods of using preshave compositions have been discovered. The present preshave compositions have chemical make-ups which provide for enhanced/increased heat generation or warming, for example, relative to one or more prior art preshaves. In addition, the present compositions can have relatively widely varying chemical make-ups, and can be employed in various preshave applications, for example, as preshave products compounded to be particularly useful and effective in benefiting one or more body areas to be shaved. For example, the present compositions may include, for example, one or more medications, such as anti-fungal agents and the like, one or more fragrances, one or more colorants and the like particularly suited for application to and benefiting of one or more body areas to be shaved.

In general, the present preshave compositions are relatively straightforward in make-up and manufacture. Such compositions are effective in use, for example, by enhancing the ease and comfort of shaving.

In one broad aspect, the present preshave compositions comprise a polyalkylene glycol component present in an amount of at least about 50% by weight of the composition; and at least one additional component in an amount effective to benefit an area of a human or animal to be shaved. The compositions are substantially clear or transparent and substantially anhydrous, and are effective to generate heat or warming when placed in contact with water, for example, when placed in contact with a living human, such as an area to be shaved of a living human.

In one embodiment, the present preshave compositions comprise an effective amount of a surfactant. The presently useful surfactants are examples of additional components effective to benefit the area to be shaved. Useful surfactants include, for example and without limitation, cationic surfactants, surfactants selected from fatty amine salts, ammonium salts, alkyl pyridinium salts, alkylamine salts, for example and without limitation, laurylamine acetate, quaternary ammonium salts, for example and without limitation, alkyltrimethyl ammonium chloride, alkyl benzyl dimethylammonium chlorides and the like and mixtures thereof, polyoxyalkylenealkylamines, such as polyoxyethylenealkylamines, and the like and mixtures thereof, and the like and mixtures thereof.

In a useful embodiment, the preshave composition may comprise one or more natural oils in an amount effective to benefit an area to be shaved. Among the natural oils useful in the present compositions are, for example and without limitation, sunflower seed oil, avocado oil, meadowfoam seed oil, kukui seed oil, grapefruit peel oil, tangerine peel oil, orange peel oil, lemon peel oil, lime peel oil, canola oil, safflower seed oil, castor oil, almond oil, sweet almond oil, chamomile oil, rosemary oil, *rosemarinus officinalis* (rosemary) leaf oil, olive oil, eucalyptus oil, *eucalyptus globus* leaf oil, peppermint oil, *mentha piperita* (peppermint) leaf oil, *lavendula angustifolia* oil, *helianthus annuus* seed oil, *cedrus atlantica* bark oil, *rosa damascena* flower oil, *cananga odorata* flower oil, *anthemis nobilis* flower oil, *amyris balsamifera* bark oil, *pelargonium graveolens* flower oil, *citrus aurantium bergamia* fruit oil, *santalum album* (sandalwood) oil, *citrus angustifolia* (bergamot) oil, *lavandula angustifolia* (lavender) oil, *salvia officinalis* (sage) oil, and the like and mixtures thereof.

The viscosities of the present compositions can be varied over a relatively wide range depending, for example, on the particular application for which the composition is to be used. For example, the present compositions can have a viscosity, at 25° C., in a range of about 50 cps or less to about 5000 cps or about 10,000 cps or more.

In one very useful embodiment, the polyalkylene glycol component, preferably a polyethylene glycol component, comprises a first polyalkylene glycol component portion having a first molecular weight and a second polyalkylene glycol component portion having a second molecular weight which is reduced relative to the first molecular weight. In one embodiment, the second molecular weight is less than about 270. A composition including both the first and second polyalkylene glycol component portions has a somewhat reduced warming or heat generating effect relative to a substantially identical composition without the second polyalkylene glycol component. However, a composition including both first and second polyalkylene glycol portions, preferably first and second polyethylene glycol portions, advantageously has a reduced cloud point temperature and/or a reduced solidification point or temperature relative to a substantially identical composition without the second polyalkylene glycol portion. Preferably, the present preshave compositions are substantially clear or substantially transparent at temperatures in a range of about 20° C. to about 30° C., for example, 25° C.

The weight ratio of the first polyalkylene glycol component portion to the second polyalkylene glycol portion may vary over a relatively wide range, for example, from about 0.1 to about 10. Such ratio may be less than about 7 or less than about 3 or less than about 1.3 or lower.

In one very useful embodiment, the second polyalkylene glycol component portion is present in a greater amount by weight than the first polyalkylene glycol component portion. For example, the second polyalkylene glycol component portion may be present in the composition in an amount in a range of about 1.1 or about 1.5 or about 2 to about 4 or about 5 or more times the amount of the first polyalkylene glycol component portion in the composition. Using an excess of the second polyalkylene glycol component portion facilitates maintaining the composition substantially clear or transparent, for example, during transportation or periods of storage or at varying temperatures, such as temperatures below room or ambient temperature, e.g., temperatures below about 22° C.

The polyalkylene glycol component, for example, the first and second polyalkylene glycol component portions combined or together, may be at least about 70% by weight or at least about 80% by weight or at least about 90% by weight of the composition. The present compositions preferably have an enhanced ability to generate heat when placed in contact with water or when placed in contact with an area to be shaved of a living human (i.e., the skin of a living human) or animal, relative to a similar or substantially identical composition containing a reduced amount, for example, at least 5% by weight less, of the polyalkylene glycol component.

The polyalkylene glycol components, and component portions, may have molecular weights varying over relatively wide ranges, for example, in a range of about 100 or about 150 to about 1000 or about 3000 or about 5000 or more. In one embodiment, first polyalkylene, for example, polyethylene, glycol component portion preferably has a molecular weight in a range of about 350 to about 450. The second polyalkylene, for example, polyethylene, glycol component portion preferably has a molecular weight in a range of about 150 to about 250.

The viscosity inducing components of the present preshave compositions may be selected from any materials or combination of materials effective to increase the viscosity, and advantageously the lubricity, of the preshave compositions, and which are compatible, that is, are substantially non-interfering, with or in the other components of the compositions and with or in the application in which the compositions are used. In one very useful embodiment, the viscosity inducing component comprises a polyvinylpyrrolidone component. Such polyvinylpyrrolidone components are effective in the present preshave compositions to increase viscosity, and to provide enhanced lubrication when in contact with an area of a body to be shaved relative to a composition, for example, a substantially identical composition, without the polyvinylpyrrolidone component. Advantageously, the polyvinylpyrrolidone component comprises a first polyvinylpyrrolidone component portion and a second polyvinylpyrrolidone component portion having a different molecular weight than the first portion. The polyvinylpyrrolidone component may further include a third polyvinylpyrrolidone component portion having a different, for example, reduced or lower, molecular weight relative to the molecular weights of both the first and second polyvinylpyrrolidone component portions.

In a particularly useful embodiment, the relative amounts of the first and second polyvinylpyrrolidone component portions, and the third polyvinylpyrrolidone component portion, if present, are selected to provide the desired viscosity and to be effective in controlling at least one, and preferably both, of the tackiness of the composition and the stringiness of the composition. For example, a composition including a high molecular weight polyvinylpyrrolidone component and no lower molecular weight polyvinylpyrrolidone component achieves a higher viscosity, but also may have an undesirable degree of tackiness and/or stringiness. Reducing the tackiness and/or stringiness of the preshave composition increases the ease of applying the composition to the area of the body to be shaved and, therefore, increases the ease of using the composition.

Compositions in accordance with the present invention which include a polyvinylpyrrolidone component portion having an average molecular weight which is different and reduced or lower, for example, in a range of about 5000 to about 15,000, relative to the molecular weight or weights of the other polyvinylpyrrolidone portion or portions present have increased viscosity relative to the composition without the lower molecular weight portion and advantageously do not have the increased stringiness of a substantially similar or identical composition having the same increased viscosity as the composition (which includes the lower molecular weight polyvinylpyrrolidone component portion) without the lower molecular weight polyvinylpyrrolidone component portion. In other words, a preshave composition in accordance with the present invention including one or more higher molecular weight polyvinylpyrrolidone component portions and a lower molecular weight polyvinylpyrrolidone component portion has increased viscosity because of the presence of the lower molecular weight portion, but does not have the increased stringiness apparent in a similar composition including no lower molecular weight polyvinylpyrrolidone component portion and having its viscosity increased by an increased amount of the one or more higher molecular weight polyvinylpyrrolidone component portions.

Each and every feature described herein, and each and every combination of two or more of such features, is included within the scope of the present invention provided that the features included in such a combination are not mutually inconsistent.

These and other aspects and advantages of the present invention will become apparent when considered in light of the following detailed description and claims.

DETAILED DESCRIPTION

The preshave compositions of the present invention are substantially anhydrous, preferably containing less than about 10% by weight of water, more preferably less than about 5% by weight of water and still more preferably containing less than about 3% by weight of water. In one very useful embodiment, the present compositions are substantially free of water. In general, all other things being equal, the smaller the amount of water present in the composition the greater the heat generating ability of the composition.

The present preshave compositions comprise a polyalkylene glycol component, which is advantageously present in a major amount by weight, that is at least about 50% by weight. The polyalkylene glycol components may include, for example and without limitation, polyalkylene glycols, polyalkylene glycol ethers, for example, polyalkylene glycol stearates, oleates, cocoates, and the like and mixtures thereof. Although, any suitable polyalkylene glycol component may be employed, advantageously, the polyalkylene glycol component is selected from polyethylene glycols (hereinafter referred to as PEG's), polyethylene glycol ethers, and the like and mixtures thereof. PEGylated compounds, such as peptide or protein derivatives obtained by PEGylation reactions may also be used. In addition, block copolymers of PEG's may be used, such as (ethyleneglycol)-block-poly(propyleneglycol)-block(polyethylene glycol), poly(ethylene glycol-propylene glycol) (ramdon copolymer) and the like and mixtures thereof. The compositions of this invention may comprise at least about 50% by weight of the polyalkylene glycol component, more preferably at least about 70%, about 80% or about 90% by weight of the composition.

In one very useful embodiment, the polyalkylene glycol component is present in different portions having different molecular weights. For example, in one embodiment the preshave compositions of the present invention comprise a first polyalkylene glycol component portion having a first molecular weight and a second polyalkylene glycol component portion having a second molecular weight reduced relative to the first molecular weight. It has been found that controlling the molecular weight of the polyalkylene glycol component and maintaining a relatively high concentration of the polyalkylene glycol component are effective in providing the present lubricant compositions with a substantially advantageous combination of benefits. For example, the present compositions provide an increased or enhanced degree of warming, for example, relative to similar compositions which have less than about 50% by weight or less than about 30% by weight of the polyalkylene glycol component. In addition, the preshave compositions are substantially clear, and a relatively wide range of desired viscosities can be easily obtained without substantial interference with other important properties, for example, lubricity, skin and/or hair conditioning, and controlled degrees of tackiness and stringiness, of the present preshave compositions. In short, in certain embodiments of the present invention it is highly advantageous to have two polyalkylene glycol component portions of differing molecular weights, the relative proportions of which are advantageously controlled to provide substantial benefits to the present compositions.

Polyalkylene glycol components, for example polyethylene glycol components, and component portions, may have molecular weights varying over relatively wide ranges, for example in a range of about 100 or about 150 to about 1000 to about 3000 or about 5000 or more. In one very useful embodiment, the first polyalkylene, for example, polyethylene, glycol component portion preferably has a molecular weight in the range of about 350 to about 450. The second polyalkylene, for example, polyethylene, glycol component portion preferably has a molecular weight of less than about 270, and more preferably in a range of about 150 to about 250. When two polyalkylene glycol component portions are used together the molecular weight difference between the two portions is preferably at least about 100 or about 150 to about 300 or about 500 or about 1000 or more.

In one very useful embodiment, the first polyethylene glycol component preferably has a molecular weight of about 350 to about 450, and is identified as PEG 400; and the second polyethylene glycol component portion has a molecular weight in a range of about 150 to about 250, and is preferably identified as PEG 200.

An important advantage of the present invention is that the present preshave compositions may have a reduced cloud point temperature relative to a similar or substantially similar composition without the second polyalkylene glycol component portion. For example, by including a second polyalkylene glycol component portion comprising PEG 200, a composition which also includes PEG 400 has a reduced cloud point temperature relative to a similar composition which includes no PEG 200, for example, which includes an amount of PEG 400 equal to the total amount of PEG 400 and PEG 200 present in the composition. Providing a preshave composition with a reduced cloud point temperature advantageously enhances the ability of the composition to remain clear or substantially clear over a broader range of temperatures.

The weight ratio of the first polyalkylene glycol component portion to the second polyalkylene glycol portion may vary over a relatively wide range, for example, from about 0.1 to about 10. Such ratio may be less than about 7 or less than about 3 or less than about 1.3 or lower, for example, less than about 1.0 or less than about 0.5 or lower.

In one very useful embodiment, the lower molecular weight second polyalkylene glycol component portion is present in a greater amount by weight than the higher molecular weight first polyalkylene glycol component portion. For example, the second polyalkylene glycol component portion such as a polyethylene glycol component portion having a relatively low molecular weight, may be present in the preshave composition in an amount in a range of about 1.1 or about 1.5 or about 2 to about 4 or about 5 or more times the amount of the first polyalkylene glycol component portion, such as a polyethylene glycol component portion having a relatively high molecular weight, in the composition. Using an excess of the second polyalkylene glycol component portion facilitates maintaining the composition substantially clear or transparent, for example, during transportation or periods of storage or at varying temperatures, such as temperatures below room or ambient temperature, e.g., temperatures below about 22° C.

The present preshave compositions further comprise at least one additional component, for example and without limitation, one or more surfactants, oils and the like and mixtures thereof, in an amount effective to benefit an area of a human or animal to be shaved. Such benefit may include, without limitation, conditioning the area, that is the skin and/or the hair located in the area, of the body to be shaved, lubricating the area of the body to be shaved, otherwise facilitating the shaving of the area of the body to be shaved, scenting the area of the body to be shaved, disinfecting and/or cleaning the area of the body to be shaved, conditioning the area, that is the skin, of the body after it is shaved, reducing razor burn and/or other irritation caused by shaving the area of the body to be shaved and the like and combinations thereof. In general, the additional components or components in the present preshave compositions, when such compositions are applied to an area of a body to be shaved allow the body area to be shaved with one or more of the following benefits: increased ease, more quickly, more completely, reduced risk of skin damage, reduced stress and the like benefits, relative to a substantially identical preshave composition without the additional component or components.

In a useful embodiment, the present preshave compositions include an effective amount of a surfactant, for example, a cationic surfactant, as an additional component. Such surfactants include, but are not limited to, fatty amine salts; ammonium salts; alkyl pyridinium salts; alkylamine salts, for example and without limitation, laurylamine acetate, and the like and mixtures thereof; quaternary ammonium salts, for example and without limitation, lauryl trimethyl ammonium chloride, alkyl benzyl dimethylammonium chlorides and the like and mixtures thereof; polyoxyethylenealkylamines and the like and mixtures thereof; and the like and mixtures thereof.

In a useful embodiment, the surfactant comprises about 1% or less or about 3% to about 10% or more by weight of the total preshave composition.

In one embodiment, the present preshave compositions may include one or more natural oils as additional components effective to benefit an area of the body to be shaved. Such natural oils include, for example and without limitation, sunflower seed oil, avocado oil, meadowfoam seed oil, kukui seed oil, grapefruit peel oil, tangerine peel oil, orange peel oil, lemon peel oil, lime peel oil, canola oil, safflower seed oil, castor oil, almond oil, sweet almond oil, chamomile oil, rosemary oil, *rosemarinus officinalis* (rosemary) leaf oil, olive oil, eucalyptus oil, *eucalyptus globus* leaf oil, peppermint oil, *mentha piperita* (peppermint) leaf oil, *lavendula angustifolia* oil, *helianthus annuus* seed oil, *cedrus atlantica* bark oil, *rosa damascena* flower oil, *cananga odorata* flower oil, *anthemis nobilis* flower oil, *amyris balsamifera* bark oil, *pelargonium graveolens* flower oil, *citrus aurantium bergamia* fruit oil, *santalum album* (sandalwood) oil, *citrus angustifolia* (bergamot) oil, *lavandula angustifolia* (lavender) oil, and *salvia officinalis* (sage) oil, and the like and mixtures thereof.

The natural oil or oils may be present in the preshave compositions in an amount effective to benefit an area of a body to be shaved. Such amounts may vary over a relatively wide range depending, for example, on the oil or oils used, the benefit or benefits to be obtained, and the like factors. For example, the natural oil or oils may be present in the present preshave compositions in a range of about 0.01% or less or about 0.1% to about 2% or about 5% or more by weight of the total preshave composition.

The present compositions may include antimicrobial agents, including but are not limited to, chlorohexidine gluconate, sodium polystyrene sulfonate, sodium cellulose sulfate, silver particles of micro- and sub-micrometer sizes, silver salts and other antibacterial agents known to the art and the like and mixtures thereof.

The present compositions may include local anesthetics, including but are not limited to, benzocaine, lidocaine, dibucaine, benzyl alcohol, camphor, resorcinol, menthol and diphenylhydramine hydrochloride and the like and mixtures thereof.

The present compositions may include plant extracts such as aloe, witch hazel, chamomile, hydrogenated soy oil and colloidal oatmeal, vitamins such as vitamins A, D or E and corticosteroids such as hydrocortisone acetate, and the like and mixtures thereof.

A preservative component may be added to guard against microbial growth. The preservative component may be selected from preservatives known to those of skill in the art, including, but not limited to, one or more of the following: methylparaben, benzoic acid, sorbic acid, gallic acid, propylparaben and the like and mixtures thereof. The preservative component may be present, if at all, in the present compositions in an amount in a range of about 0.01% or less to about 0.5% or more by weight.

The present compositions may, and advantageously do, include an effective amount of a viscosity inducing component. As noted elsewhere herein, the viscosity inducing component may be selected from any material or combination of materials effective to increase, preferably controllably increase, the viscosity of the composition. The presently useful viscosity inducing components advantageously are compatible, that is are substantially non-interfering with or in the other components of the composition and with or in the application in which the composition is used. In one embodiment, the viscosity inducing component is other than a cellulosic derivative, although in other of the present lubricant compositions cellulosic derivatives may be employed. In one embodiment, the present compositions are substantially free of any cellulosic derivatives.

In a very useful embodiment of the present invention, the viscosity inducing component comprises a polyvinylpyrrolidone component. Such polyvinylpyrrolidone (PVP) component is very effective in providing controlled increases in viscosity at relatively low concentrations while, at the same time, providing increases in lubricity to the present compositions.

Advantageously, the PVP component comprises a first PVP component portion and a second PVP component portion having a different molecular weight than the first portion. The PVP component may include a third PVP component portion having a different, and preferably reduced, molecular weight than both the first and second PVP component portions. The relative amounts of the first and second, and third if present, PVP component portions may be selected to be effective in controlling at least one, and preferably both, of the tackiness of the composition and the stringiness of the composition. The tackiness and/or stringiness of the present compositions are of substantial importance, for example, when the composition is applied to the skin. In addition, even as a stand-alone lubricant product, for example, for use as a personal lubricant, the present compositions advantageously have controlled tackiness and/or controlled stringiness to be an esthetically pleasing product, for example, being substantially uniform and/or smooth and/or having a substantially consistent texture when applied to the human or animal body. Preferably, the compositions of the present invention contain about 1% to about 15%, more preferably about 2% to about 10% by weight of the viscosity inducing component, for example, the PVP component.

In the event that a first viscosity inducing component portion and a second viscosity inducing component portion having a reduced molecular weight relative to the first portion are employed in the present preshave compositions, the relative amounts of the first and second portions may vary over a relatively wide range, for example, to facilitate providing a composition having the desired properties for any one of a number of relatively widely varying applications. For example, the weight ratio of first portion to second portion may range from about 0.05 or about 0.1 to about 0.3 or about 0.5 or about 1 or higher. In the event first and second PVP portions are employed, the weight ratio of first portion to second portion is advantageously in the range of about 0.1 to about 0.3.

The molecular weight of the viscosity inducing component may be in a range of about 5000 or less or about 10,000 to about 100,000 or about 1,500,000 or higher.

In one embodiment, the present compositions include a first PVP component portion having a molecular weight in a range of about 100,000 to about 1,500,000 or higher, for example, about 300,000 to about 1,000,000; and a second PVP component portion having an average molecular weight in a range of about 25,000 to about 90,000, for example, about 35,000 to about 55,000. A reduced or lower molecular weight, for example, a third, PVP component portion may be present, as discussed elsewhere herein, and advantageously have an average molecular weight of about 3000 to about 20,000, for example, about 5,000 to about 15,000.

The present preshave compositions increase in temperature upon exposure to moisture from the skin, without causing undue irritation or harm to the skin surfaces. This warming occurs by the exothermic release of energy generated upon exposing the compositions to water. The temperature increase advantageously falls within a comfort range from the minimum perceptible temperature increase to no more than that perceived as too hot, for example, causing irritation or other harm to the skin or mucosa.

Without wishing to limit the invention to any particular theory of operation, it is believed that the polyalkylene glycol components in the present preshave compositions are useful as warming or heat-generating agents. The viscosity inducing component is useful to increase, preferably controllably increase the viscosity of the preshave composition. The present compositions are advantageous in that they lubricate, warm, and soothe the tissues of the user, especially the skin of the user. Moreover, they are advantageously smooth and lubricating, rather than being stringy and tacky.

The compositions of the present invention may further include a variety of ingredients known in the preshave art. Examples of such ingredients include, without limitation, fragrances, colorants, hair and/or skin conditioners and the like and mixtures thereof. Such ingredients may be included in an effective amount to achieve the desired result/benefit. Such amounts are similar to the amounts of such ingredients used in conventional preshave compositions.

The present compositions may be in the form of a liquid, a semi-solid, or a solid depending upon the particular intended use or application thereof. The present compositions may be formulated as syrupy liquid-gels pourable gels or thick jellies or as pourable liquids. Preferably, the viscosities are in a range of about 50 cps or about 100 cps to less than about 500 cps or less than about 1000 cps or less than about 2000 cps. However, as noted above, viscosities in the present compositions may range from about 1000 cps to about 10,000 cps for gel, and from 60,000 cps to about 500,000 cps or more for the jellies. The present compositions may also be formulated into soft or hard gelatin capsules, or may be impregnated into fabrics or polymers.

The present preshave compositions are often effective to convey a feeling of warmth. The feeling of warmth generated by the compositions of this invention is soothing to the skin areas to which the compositions are applied. The compositions of the invention may also possess a sweet and pleasant taste, and may optionally include effective amounts of sweetening agents and/or flavoring agents which are of particular benefit when these compositions are accidentally ingested.

The compositions of this invention are preferably applied to an area to be shaved (e.g., the skin and hair to be shaved) prior to shaving (e.g., prior to shaving the hair off the skin with a razor and/or prior to the application of shaving creams or lotions intended to be used during such shaving). Prior to applying the present compositions, the area of the body to be shaved may be wet or dry. The area to be shaved includes any area of the body, that is a human or animal body, that contains hair, for example, the face and/or neck areas, the scalp, the chest, the underarms, the legs, the arms, the back, the feet, the hands, and the pubic area.

The preshave compositions of the present invention may be left on the body area to be shaved during shaving, or may be removed prior to shaving, either by hand washing or by mechanical means, for example, using a dry or wet cloth or towel. The preshave compositions are preferably left on the area to be shaved for at least an amount of time sufficient to benefit the area to be shaved, for example, for at least about 1, 2, 3, 4 or about 5 to about 15 or about 20 or more minutes. The present compositions may be applied to the skin at least about 1, 2, 3, 4 or about 5 minutes before commencing the actual shaving operation.

The area of the body to be shaved may be shaved using any suitable shaving instrument and/or technique, for example and without limitation an electric razor, a mechanical blade razor, that is a razor with one, two, three, four or more blades, and the like and combinations thereof. Other materials, such as shaving creams, gels and lotions, as well as after shave products can be used in conjunction with the present preshave compositions, for example, in a manner similar to how such other material or materials are used in conjunction with conventional or other preshave compositions.

The following non-limiting examples illustrate certain aspects of the present invention.

EXAMPLES 1 TO 8

A series of eight (8) compositions were prepared for testing. These compositions were anhydrous and had chemical make-ups as shown in Table 1. The compositions were formed by combining or blending the ingredients together and stirring or mixing to obtain a uniform composition. The compositions of the present invention preferably are made from NF grade materials, which reduce the toxicity of the compositions.

TABLE 1

| | COMPOSITIONS | | | | | | | |
|---|---|---|---|---|---|---|---|---|
| INGREDIENT | 1 | 2 | 3 | 4 | 5 | 6 | 7 | 8 |
| % by wt | % by wt | % by wt | % by wt | % by wt | % by wt | % by wt | % by wt | % by wt |
| PEG 400 (A) | 91.0 | 93.0 | 89.0 | 65.4 | 83.35 | 50.0 | 26.55 | 24.0 |
| PEG 200 (B) | — | — | — | 25.0 | 12.50 | 45.5 | 70.8 | 0.25 |
| BUTYLENE GLYCOL | — | — | — | — | — | — | — | — |
| LUVISKOL K90 (C) | 9.0 | 7.0 | 1.0 | 0.8 | — | — | — | — |
| LUVISKOL K30 (D) | — | — | 10.0 | 8.8 | — | — | — | — |
| KOLLIDON K17 (E) | — | — | — | — | — | — | 0.25 | 0.5 |
| KOLLIDON 30 (F) | — | — | — | — | 3.75 | 3.75 | 2.0 | 4.0 |
| KOLLIDON 90F (G) | — | — | — | — | 0.40 | 0.75 | 0.4 | 1.25 |

TABLE 1-continued

| INGREDIENT % by wt | 1 % by wt | 2 % by wt | 3 % by wt | 4 % by wt | 5 % by wt | 6 % by wt | 7 % by wt | 8 % by wt |
|---|---|---|---|---|---|---|---|---|
| | | | | COMPOSITIONS | | | | |
| VISCOSITY cps @25 °C. | 10,800 | 5400 | 3250 | 1400 | 350 | 450 | 550-650 | 500-650 |

(A) Polyethylene glycol having a molecular weight of about 400 (Sold by BASF) (Equivalent products produced by Dow Chemical)
(B) Polyethlyene glycol having a molecular weight of about 200 (Sold by BASF) (Equivalent products produced by Dow Chemical)
(C) Polyvinylpyrrolidone having an average molecular weight of about 300,000-1,000,000 or about 360,000 (Sold by BASF) (Equivalent products produced by ISP).
(D) Polyvinylpyrrolidone having an average molecular weight of about 35,000-55,000 or about 40,000 (Sold by BASF) (Equivalent products produced by ISP).
(E) Polyvinylpyrrolidone having an average molecular weight of about 5,000-15,000 or about 10,000 (Sold by BASF) (Equivalent products produced by ISP).
(F) Polyvinylpyrrolidone having an average molecular weight of about 35,000-55,000 or about 40,000 (Sold by BASF) (Equivalent products produced by ISP).
(G) Polyvinylpyrrolidone having an average molecular weight of about 300,000-1,000,000 or about 360,000 (Sold by BASF) (Equivalent products produced by ISP).

EXAMPLES 9 TO 16

Each of the Compositions 1 to 8 is tested for heat generation efficacy relative to a commercially available product, in particular KY Warming Lubricant. Briefly, 50 grams of each of the Compositions 1 to 7 and KY Warming Lubricant is placed in a container holding 50 grams of water. Each mixture is stirred. The temperature of each mixture is monitored until the temperature reaches a steady value. That temperature is noted.

The temperature noted in this test with each of the Compositions 1 to 8 is higher than the temperature in the test with KY Warming Lubricant.

These results indicate that each of the Compositions 1 to 8 provide enhanced heat generation relative to KY Warming Lubricant.

It should be noted that the maximum temperature increase obtained by any warming lubricant varies depending on how much lubricant is used and the individual application in which the lubricant is used, among other factors. The tests and results presented here do, however, demonstrate that the Compositions 1 to 8 provide increased heat generation, on a per unit weight basis, relative to KY Warming Lubricant.

EXAMPLES 17 TO 20

Compositions 5, 6, 7 and 8 are each augmented with 1.0% by weight of each of two cationic surfactants, namely Cetrimonium bromide and Disoydimonium chloride. Cetrimonium bromide is also known as Cetrimide and is considered an antiseptic.

Each of these compositions is used daily for two weeks as a preshave for facial hair by an adult human male. Such use involved applying the composition to the area of the face to be shaved. About two minutes after the composition is applied, and with the composition still on the area, the area is shaved, using a conventional electrical razor, to remove the facial hair. After shaving, the face is rinsed with warm water to remove the composition.

At the end of the two week period, each human male reported a reduction in or even elimination of, typical razor burn experienced while shaving without pretreatment with the present compositions. In addition, each of the male humans reported that blemishes on his face actually cleared up during the two week period, and that closer shaves were obtained during the two week period.

EXAMPLES 21 TO 23

A series of three (3) preshave compositions are prepared for testing. These compositions were anhydrous and had chemical make-ups as shown in Table 2. The preshave compositions were formed by combining or blending the ingredients together and stirring or mixing to obtain a uniform composition. The ingredients used to produce these compositions are NF grade materials.

TABLE 2

| INGREDIENT | PRESHAVE COMPOSITIONS | | |
|---|---|---|---|
| % by wt | 21 | 22 | 23 |
| PEG 400 (A) | 49.0 | 24.0 | 24.0 |
| PEG 200 (B) | 43.0 | 70.50 | 73.0 |
| KOLLIDON 30 (F.) | 6.0 | 3.5 | 1.0 |
| CETRIMONIUM BROMIDE(H) | 1.0 | 1.0 | 1.0 |
| DISOYDIMONIUM CHLORIDE | 1.0 | 1.0 | 1.0 |
| PEPPERMINT OIL | 0.05 | 0.05 | 0.05 |
| VISCOSITY cps @ °25 C. | 150 | 100 | 50 |

(H) Chemical Name - Hexadecyltrimethylammonium bromide

EXAMPLES 24-26

Each of the compositions 21, 22 and 23 is used daily for two weeks as a preshave for facial hair by an adult human male. Such use involved applying the composition to the area of the face to be shaved. About two minutes after the composition is applied, and with the composition still on the area, the area is shaved, using a conventional electric razor, to remove the facial hair. After shaving, the face is rinsed with warm water to remove the composition.

At the end of the two week period, each human male reported a reduction in or even elimination of typical razor burn experienced while shaving without pretreatment with the present composition. In addition, each of the male humans reported that blemishes on his face actually cleared up during the two week period, and that closer shaves were obtained during the two week period.

While this invention has been described with respect to various specific examples and embodiments, it is to be understood that the invention is not limited thereto and that it can be variously practiced within the scope of the following claims.

What is claimed is:

1. A preshave composition comprising:
a first polyalkylene glycol component portion having an average molecular weight a range of about 350 to about 450 and a second polyalkylene glycol component portion having an average molecular weight in a range of about 150 to about 250,
wherein said first and second polyalkylene glycol component portions comprise the same polyalkylene glycol and said first and second polyalkylene glycol component portions together comprise at least about 50% by weight of the composition; a cationic surfactant; and at least one additional component in an amount effective to benefit an area of a human or animal to be shaved, said at least one additional component comprising a natural oil; the composition being substantially clear and substantially anhydrous, and being effective to generate heat when placed in contact with water,
wherein said preshave composition has a reduced cloud point temperature relative to a substantially identical preshave composition without the second polyalkylene glycol component portion.

2. The composition of claim 1, wherein the second polyalkylene glycol component portion is present in a greater amount by weight than the first polyalkylene glycol component portion.

3. The composition of claim 1 wherein the first and second polyalkylene glycol component portions comprises a polyethylene glycol.

4. The composition of claim 1, comprising a surfactant selected from the group consisting of fatty amine salts, ammonium salts, alkyl pyridinium salts, alkylamine salts, quaternary ammonium salts, polyoxyalkylenealkylamines and mixtures thereof.

5. The composition of claim 1, comprising a surfactant selected from the group consisting of laurylamine acetate, lauryl trimethyl ammonium chloride, alkyl benzyl dimethylammonium chlorides and mixtures thereof.

6. The composition of claim 1, wherein the at least one additional component comprises an oil selected from the group consisting of: sunflower seed oil, avocado oil, meadowfoam seed oil, kukui seed oil, grapefruit peel oil, tangerine peel oil, orange peel oil, lemon peel oil, lime peel oil, canola oil, safflower seed oil, castor oil, almond oil, sweet almond oil, chamomile oil, rosemary oil, *rosemarinus officinalis* (rosemary) leaf oil, olive oil, eucalyptus oil, *eucalyptus globus* peppermint oil, *mentha piperita* (peppermint) oil, *helianthus annuus* flower oil, *cedrus atlantica* bark oil, *rosa damascena* flower oil, *cananga odorata* flower oil, *anthemis nobilis* flower oil, *amyris balsamifera* bark oil, *pelargonium graveolens* flower oil, *citrus aurantium bergamia* fruit oil, *santalum album* (sandalwood) oil, *citrus angustifolia* (bergamot) oil, *lavandula angustifolia* (lavender) oil, and *salvia officinalis* (sage) oil and mixtures thereof.

7. The composition of claim 1, having a viscosity in a range of about 50 cps to less than 10,000 cps at 25° C.

8. The composition of claim 1, which further comprises an effective amount of a viscosity inducing component other than a cellulosic derivative.

9. The composition of claim 8, wherein the viscosity inducing component comprises a polyvinylpyrrolidone component.

10. The composition of claim 9 wherein the polyvinylpyrrolidone component comprises a first polyvinylpyrrolidone component portion and a second polyvinylpyrrolidone component portion having a different average molecular weight than the first portion.

11. The composition of claim 10, wherein the polyvinylpyrrolidone component includes a third polyvinylpyrrolidone component portion having a different average molecular weight than both the first and second portions.

12. A preshave composition comprising:
a first polyalkylene glycol component portion having an average molecular weight in a range of about 350 to about 450 and a second polyalkylene glycol component portion having an average molecular weight in a range of about 150 to about 250, wherein said first and second polyalkylene glycol component portions comprise the same polyalkylene glycol and said first and second polyalkylene glycol component portions together comprise at least about 50% by weight of the composition; a cationic surfactant; and at least one additional component in an amount effective to benefit an area to be shaved; and
an effective amount of a viscosity inducing component comprising a polyvinylpyrrolidone component,
the composition being substantially clear and substantially anhydrous, and being effective to generate heat when placed in contact with water and wherein said preshave composition has a reduced cloud point temperature relative to a substantially identical preshave composition without the second polyalkylene glycol portion.

13. The composition of claim 12, wherein the second polyalkylene glycol component portion is present in a greater amount by weight than the first polyalkylene glycol component portion.

14. The composition of claim 12, wherein the at least one additional component comprises a cationic surfactant.

15. The composition of claim 12, wherein the at least one additional component comprises a surfactant selected from the group consisting of fatty amine salts, ammonium salts, alkyl pyridinium salts, alkylamine salts, quaternary ammonium salts, polyoxyalkylenealkylamines and mixtures thereof.

16. The composition of claim 12, wherein the at least one additional component comprises a surfactant selected from the group consisting of laurylamine acetate, lauryl trimethyl ammonium chloride, alkyl benzyl dimethylammonium chlorides and mixtures thereof.

17. The composition of claim 12, wherein the at least one additional component comprises a natural oil.

18. The composition of claim 12, wherein the at least one additional component comprises an oil selected from the group consisting of: sunflower seed oil, avocado oil, meadowfoam seed oil, kukui seed oil, grapefruit peel oil, tangerine peel oil, orange peel oil, lemon peel oil, lime peel oil, canola oil, safflower seed oil, castor oil, almond oil, sweet almond oil, chamomile oil, rosemary oil, *rosemarinus officinalis* (rosemary) leaf oil, olive oil, eucalyptus oil, *eucalyptus globus* leaf oil, peppermint oil, *mentha piperi* to (peppermint) leaf *lavendula angustifolia* oil, *helianthus annuus* seed oil, *cedrus atlantica* bark oil, *cananga odorata* flower oil, *anthemis nobilis* flower oil, *amyris balsamifera* bark oil, pelargonium seed oil, *rosa damascena* flower oil, graveolens flower oil, *citrus aurantium* bergamia fruit oil, santalum album (sandalwood) oil, *citrus angustifolia*(bergamot) oil, *lavandula angustifolia* (lavender) oil, and *salvia officinalis* (sage) oil, and mixtures thereof.

19. The composition of claim 12, having a viscosity in a range of about 50 cps to less than 10,000 cps at 25° C.

20. The composition of claim 12, wherein the polyvinylpyrrolidone component comprises a first polyvinylpyrrolidone component portion and a second polyvinylpyrrolidone component portion having a different average molecular weight than the first portion.

21. The composition of claim 20, wherein the polyvinylpyrrolidone component includes a third polyvinylpyrrolidone component portion having a different average molecular weight than both the first and second portions.

22. A method of preparing an area of a human or animal body to be shaved comprising:
    contacting an area of a human or animal body to be shaved with an effective amount of the preshave composition of claim 1.

23. The method of claim 22, wherein the area to be shaved is selected from the group consisting of: face, neck, back, chest, scalp, underarm, leg, bikini area and combinations thereof.

24. The method of claim 22, wherein the preshave composition is removed from the area to be shaved prior to shaving the area.

25. The method of claim 22, wherein the preshave composition is washed from the area to be shaved using water.

26. The method of claim 22, wherein the preshave composition is removed from the area to be shaved using a dry cloth or towel.

27. The method of claim 22, wherein the preshave composition is not removed from the area prior to shaving.

28. The method of claim 22, wherein the preshave composition is left on the area for at least about 1 minute prior to shaving the area.

29. The method of claim 22, wherein the preshave composition is left on the area for about 5 minutes or less prior to shaving the area.

30. A method of preparing an area of a human or animal body to be shaved comprising:
    contacting an area of a human or animal body to be shaved with an effective amount of the preshave composition of claim 12.

31. The method of claim 30, wherein the area to be shaved is selected from the group consisting of: face, neck, back, chest/scalp, underarm, leg, bikini area and combinations thereof.

32. The method of claim 30, wherein the preshave composition is removed from the area to be shaved prior to shaving the area.

33. The method of claim 30, wherein the preshave composition is not removed from the area prior to shaving.

34. The method of claim 30, wherein the preshave composition is left on the area for at least about 1 minute prior to shaving the area.

35. The method of claim 30, wherein the preshave composition is left on the area for about 5 minutes or less prior to shaving the area.

* * * * *